(12) United States Patent
Meyer (10) Patent No.: US 9,095,425 B2
(45) Date of Patent: Aug. 4, 2015

(54) MODULAR INTRAOCULAR LENS INJECTOR

(75) Inventor: Rolf Meyer, Port (CH)

(73) Assignee: ASICO, LLC, Westmont, IL (US)

( * ) Notice: Subject to any disclaimer, the term of this patent is extended or adjusted under 35 U.S.C. 154(b) by 141 days.

(21) Appl. No.: 13/605,456

(22) Filed: Sep. 6, 2012

(65) Prior Publication Data

US 2013/0060257 A1    Mar. 7, 2013

(30) Foreign Application Priority Data

Sep. 7, 2011   (EP) ..................................... 11180329

(51) Int. Cl.
   *A61F 2/16*   (2006.01)

(52) U.S. Cl.
   CPC ............... *A61F 2/167* (2013.01); *A61F 2/1678* (2013.01)

(58) Field of Classification Search
   CPC ..... A61F 2/167; A61F 2/1678; A61F 2/1662; A61F 2/1664; A61F 2/1667; A61F 2/1672; A61F 2/1675
   USPC .......................... 606/107; 623/6.11, 6.12, 6.41
   See application file for complete search history.

(56) References Cited

U.S. PATENT DOCUMENTS

| | | | | |
|---|---|---|---|---|
| 2,833,280 | A * | 5/1958 | Hein, Jr. ........................... | 604/89 |
| 3,640,278 | A * | 2/1972 | Friedman ....................... | 604/192 |
| 3,951,146 | A * | 4/1976 | Chiquiar-Arias ............. | 604/110 |
| 4,206,768 | A * | 6/1980 | Bailey .......................... | 600/576 |
| 4,407,283 | A * | 10/1983 | Reynolds ...................... | 604/136 |
| 4,747,404 | A * | 5/1988 | Jampel et al. ................. | 606/107 |
| 4,852,566 | A * | 8/1989 | Callahan et al. ............... | 606/107 |
| 4,880,000 | A * | 11/1989 | Holmes et al. ................. | 606/107 |
| 4,931,043 | A * | 6/1990 | Ray et al. ....................... | 604/228 |
| 4,934,363 | A * | 6/1990 | Smith et al. .................... | 606/107 |
| 4,955,889 | A | 9/1990 | Van Gent | |
| 5,059,179 | A * | 10/1991 | Quatrochi et al. ............. | 604/110 |

(Continued)

FOREIGN PATENT DOCUMENTS

| EP | 0 270 257 A1 | 6/1988 |
|---|---|---|
| EP | 1 832 247 A1 | 9/2007 |

(Continued)

OTHER PUBLICATIONS

European Search Report dated Nov. 27, 2012, issued in European Patent Application No. 11180329.2.

(Continued)

*Primary Examiner* — Ryan Severson
*Assistant Examiner* — Christian Knauss
(74) *Attorney, Agent, or Firm* — Wood, Phillips, Katz, Clark & Mortimer (57) ABSTRACT

An injector for inserting an intraocular lens into an eye, comprising a main body (10) and a plunger (50). A guide element (30) is connected to the distal end of the plunger to laterally guide the plunger during movement along a longitudinal axis (L). The distal end of the guide element has a structure for fastening a plunger needle to the guide element. A radial guide pin (40) is in aligned radial bores of the guide element and plunger and extends into a longitudinal slot (17) of the main body to prevent twisting and to secure the guide element to the plunger. A retaining element (24) interacts with a running surface on the perimeter of the plunger, the running surface having a variable radial distance from the longitudinal axis so as to cause an axial resistance force which depends on the axial position of the plunger.

22 Claims, 3 Drawing Sheets

(56) References Cited

U.S. PATENT DOCUMENTS

| | | | |
|---|---|---|---|
| 5,066,297 A * | 11/1991 | Cumming | 606/107 |
| 5,098,439 A * | 3/1992 | Hill et al. | 606/107 |
| 5,106,372 A * | 4/1992 | Ranford | 604/110 |
| 5,139,508 A * | 8/1992 | Kantrowitz et al. | 606/184 |
| 5,171,313 A * | 12/1992 | Salyer | 606/86 R |
| 5,190,552 A * | 3/1993 | Kelman | 606/107 |
| 5,236,433 A * | 8/1993 | Salyer | 606/91 |
| 5,250,026 A * | 10/1993 | Ehrlich et al. | 604/60 |
| 5,304,182 A * | 4/1994 | Rheinish et al. | 606/107 |
| 5,427,088 A * | 6/1995 | Graether | 600/236 |
| 5,494,484 A * | 2/1996 | Feingold | 606/107 |
| 5,616,148 A * | 4/1997 | Eagles et al. | 606/107 |
| 5,620,450 A * | 4/1997 | Eagles et al. | 606/107 |
| 5,643,276 A * | 7/1997 | Zaleski | 606/107 |
| 5,772,666 A * | 6/1998 | Feingold et al. | 606/107 |
| 5,807,400 A | 9/1998 | Chambers et al. | |
| 5,860,984 A * | 1/1999 | Chambers et al. | 606/107 |
| 6,203,549 B1 * | 3/2001 | Waldock | 606/107 |
| 6,312,410 B1 * | 11/2001 | Yamamoto | 604/152 |
| 7,097,649 B2 | 8/2006 | Meyer | |
| 2002/0165610 A1 * | 11/2002 | Waldock | 623/6.12 |
| 2003/0040755 A1 * | 2/2003 | Meyer | 606/107 |
| 2003/0120199 A1 * | 6/2003 | Sussman et al. | 604/22 |
| 2004/0054374 A1 * | 3/2004 | Weber et al. | 606/107 |
| 2004/0059343 A1 * | 3/2004 | Shearer et al. | 606/107 |
| 2004/0097954 A1 * | 5/2004 | Meyer | 606/107 |
| 2004/0199173 A1 * | 10/2004 | Meyer | 606/107 |
| 2004/0215133 A1 * | 10/2004 | Weber et al. | 604/60 |
| 2005/0149057 A1 | 7/2005 | Rathert | |
| 2005/0154399 A1 * | 7/2005 | Weber et al. | 606/107 |
| 2006/0085013 A1 * | 4/2006 | Dusek et al. | 606/107 |
| 2006/0167466 A1 * | 7/2006 | Dusek | 606/107 |
| 2006/0235429 A1 * | 10/2006 | Lee et al. | 606/107 |
| 2007/0005135 A1 * | 1/2007 | Makker et al. | 623/6.12 |
| 2007/0150056 A1 * | 6/2007 | Meyer | 623/6.12 |
| 2008/0086146 A1 * | 4/2008 | Ishii et al. | 606/107 |
| 2008/0097459 A1 * | 4/2008 | Kammerlander et al. | 606/107 |
| 2008/0255579 A1 * | 10/2008 | Wollenhaupt et al. | 606/107 |
| 2009/0036898 A1 * | 2/2009 | Ichinohe et al. | 606/107 |
| 2009/0112223 A1 * | 4/2009 | Downer et al. | 606/107 |
| 2009/0118738 A1 * | 5/2009 | Gerondale | 606/107 |
| 2009/0216244 A1 * | 8/2009 | Pynson | 606/107 |
| 2009/0240257 A1 * | 9/2009 | Meyer | 606/107 |
| 2009/0292293 A1 * | 11/2009 | Bogaert et al. | 606/107 |
| 2009/0292294 A1 * | 11/2009 | Tanaka | 606/107 |
| 2010/0185205 A1 * | 7/2010 | Novakovic et al. | 606/107 |
| 2010/0222674 A1 * | 9/2010 | Cowan et al. | 600/432 |
| 2010/0305577 A1 * | 12/2010 | Muchhala et al. | 606/107 |
| 2010/0312254 A1 | 12/2010 | Downer et al. | |
| 2011/0094599 A1 * | 4/2011 | Meyer | 137/15.04 |
| 2011/0172676 A1 * | 7/2011 | Chen | 606/107 |
| 2011/0257658 A1 * | 10/2011 | Chen et al. | 606/107 |
| 2011/0270264 A1 * | 11/2011 | Shoji et al. | 606/107 |

FOREIGN PATENT DOCUMENTS

| | | |
|---|---|---|
| EP | 1 857 076 A2 | 11/2007 |
| EP | 2161005 A1 | 3/2010 |
| EP | 2340786 A1 | 7/2011 |
| WO | 2010/039841 A1 | 4/2010 |

OTHER PUBLICATIONS

Partial European Search Report of EP 11 18 0329 dated Jun. 21, 2012.

* cited by examiner

MODULAR INTRAOCULAR LENS INJECTOR

TECHNICAL FIELD

The present invention relates to an apparatus for inserting an artificial intraocular lens into the eye of a patient during cataract surgery. This type of device is often generally referred to as an intraocular lens injector.

PRIOR ART

In cataract surgery, an opaque natural lens in a patient's eye is replaced by an artificial intraocular lens (IOL). In this procedure, the natural lens is first removed, usually by phacoemulsification. Then the artificial IOL is inserted. A variety of techniques can be used for the insertion step. Traditionally, surgeons have introduced the lens into the eye with the aid of surgical forceps. Alternatively, a specifically adapted insertion apparatus, in the following referred to as an IOL injector, may be used. Such a device generally comprises a sleeve-like main body and a plunger longitudinally displaceable within the main body for advancing an IOL in a deformed (e.g., rolled or folded) state through a small-diameter nozzle into the patient's eye. The lens is then allowed to unfold in the eye. The nozzle, which is introduced into the eye through a small incision, often has a diameter of no more than 1.5 millimeters.

A variety of different injectors have become known in the art. In some examples, the plunger is connected to the main body via a thread. The plunger is advanced longitudinally by rotating a proximal end of the plunger, the thread translating the rotation into a longitudinal displacement. While such a device does permit exact guiding of the plunger, the surgeon needs both hands for operating the device, and it is relatively difficult to hold the device straight during operation.

Therefore, syringe-like injectors have been devised which permit one-handed operation. These devices comprise a slidable plunger which can be advanced by simply pushing on a proximal plunger head. In use, the surgeon holds the main body between his index finger and middle finger, while he presses on the plunger head with the thumb of the same hand to advance the plunger in the main body. This is a very delicate operation requiring extremely fine control. In particular, it must be avoided that the surgeon "overshoots", whereby the deformed lens would shoot out of the nozzle in an uncontrollable manner.

For improving control, various means for guiding the plunger in the main body have been devised.

U.S. Pat. No. 7,097,649 discloses an IOL injector comprising a main body and a plunger movably disposed in the main body. The plunger is guided in the main body by means of a ball bearing bush arranged in the rear part of the main body. The plunger is provided with a rectilinear guide groove. In the ball bearing bush or outside of the ball bearing bush, a guide element in the form of a spring-loaded sphere is provided to keep the plunger rotationally fixed relative to the main body.

U.S. Pat. No. 6,203,549 discloses an instrument for the insertion of an intraocular lens into an eye, with a main body, a plunger and a center rod (plunger needle). The center rod is fitted into a central hole drilled into the forward end of the plunger and held in position by friction welding. At two positions along its length, the plunger has circumferential grooves which carry bushes for guiding the plunger in the main body. A stop pin extends radially through the wall of the main body at its rearward end and projects into a groove in the plunger, acting to keep the plunger rotationally fixed and serving as a stop to limit movement of the plunger both forwards and rearwards.

U.S. Pat. No. 5,807,400 discloses an instrument for the insertion of an intraocular lens into an eye, with a main body and a plunger displaceable therein. The plunger comprises two portions, which can have a one-piece construction or can be made as two separate pieces connected together in some suitable manner, e. g., by an interference fit, a snap fit or a keyway type connection. The rearward portion of the plunger has a cross-shaped cross section and is guided in the main body in a plunger guide having a likewise cross-shaped cross section to prevent relative rotation of the plunger and the main body.

US 2010/312254 discloses an intraocular lens delivery system including an injector body having a bore surrounded by an inner wall. The system further includes a plunger configured to fit within the bore. The system also includes a plurality of deflectable members connected to the plunger and configured to contact the inner wall and to be deflected when the plunger is inserted within the bore. The deflectable members center the plunger and contribute to producing a predetermined force resisting advancement of the plunger.

US 2010/305577 discloses an intraocular lens delivery system with a multi-segment plunger, including a disposable plunger tip segment (plunger needle) that can be attached and removed from a reusable plunger base segment through a twist-lock type connection.

WO 2010/039841 discloses an IOL injector, comprising an injector body, a plunger and a plunger collar. The plunger comprises a plunger body, a plunger shaft and a plunger tip. The collar comprises a hole or a channel, the plunger shaft extending therethrough. The plunger shaft is slidably, frictionally engaged with the collar. The plunger and the collar are arranged within a lumen of the injector body such that an outer surface of the collar can smoothly slide within the lumen wall from a first location where the tip is proximal of an IOL disposed at the loading bay to a second location where the stop interferes with the collar. The collar has an outer dimension that is substantially equal to a dimension of the lumen so as to rotationally lock the plunger relative to the injector body.

SUMMARY OF THE INVENTION

It is an object of the present invention to provide an IOL injector which has a simple construction while providing excellent guidance of the plunger in the main body.

This object is achieved by an apparatus having the features of claim 1 or of claim 14. Further embodiments of the invention are laid down in the dependent claims.

Thus, in a first aspect, the present invention provides an apparatus for inserting an intraocular lens into an eye, comprising:

a main body having a barrel portion defining a passage (which is preferably delimited by a cylindrical inner surface of a sidewall of the barrel portion) extending along a longitudinal axis; and a plunger movably received in said passage, the plunger having a distal end and having a proximal end (or plunger head) for manually pressing the plunger forward in the main body along the longitudinal axis; and a guide element connected to the distal end of said plunger, the guide element being a separate structure from said plunger, the guide element laterally guiding the plunger during movement along the longitudinal axis (preferably by direct contact between the guide element and an inner surface of the barrel portion), the guide element having a proximal end and a distal end, the distal end of the guide element having a fastening structure for fastening a plunger needle to said guide element.

The guide element thus fulfills a double purpose. In a first aspect, the guide element guides the plunger for axial movement in the main body, while at the same time, in a second aspect, the guide element releasably carries the plunger needle, which generally is a disposable part which is exchanged after each use.

In the simplest case, the fastening structure may comprise a first longitudinal bore in the guide element, the first longitudinal bore being open towards the distal end of the guide element. The plunger needle may then simply be held in the bore by a friction fit. In other embodiments, it may be screwed into the bore via a threaded connection, or a bayonet-type or twist-lock coupling may be provided.

The guide element may have a second longitudinal bore which is open towards the proximal end of the guide element. The two bores may be blind holes or may be connected to form a single through-bore. The plunger then preferably has a distal fastening portion extending into the second longitudinal bore.

For securing the plunger against rotation, the barrel portion of the main body may be provided with a substantially longitudinal internal groove in an inner surface of the barrel portion or with a substantially longitudinal slot in a sidewall of the barrel portion, and the guide element may carry a laterally protruding stop element extending laterally into said groove or slot so as to prevent twisting of the plunger relative to the main body. In this case, the guide element even takes on a triple function: guiding the plunger, holding the plunger needle, and securing the plunger against rotation. These three functions are united in a single element in a very simple and elegant fashion, enabling the injector to be assembled and disassembled (e.g. for cleaning purposes) in an extremely simple fashion while providing excellent control to the surgeon.

In a particularly advantageous embodiment, the guide element has a radial bore, and the stop element comprises (preferably, consists of) a guide pin extending into said radial bore. In this case, it is preferred that the plunger has a distal fastening portion connected to said guide element, the fastening portion also having a radial bore, that the bore of the fastening portion is in alignment with the radial bore of the guide element, and that the stop element extends both into the radial bore of the guide element and into the radial bore of the fastening portion so as to lock the plunger relative to the guide element. In this case, the stop element takes on a double function: securing the plunger against unwanted rotation, and locking the plunger to the guide element.

In a particularly simple embodiment, the guide pin has a substantially cylindrical portion extending into the radial bore of the guide element and a flange portion having an increased diameter relative to the cylindrical portion, the flange portion extending into said groove or slot of the main body.

The guide element and the barrel portion of the main body (in particular, the outer surface of the guide element and a cylindrical inner surface of the barrel portion) together preferably form a linear friction bearing (i.e. a linear plain bearing) for the plunger. However it is also conceivable to provide one or more ball bearings on the outside of the guide element.

In the case of a friction bearing, the guide element preferably has a cylinder portion defining, with its peripheral outer surface, a substantially cylindrical bearing surface, said bearing surface being in direct contact with an inner surface of the barrel portion of the main body. However, the bearing surface need not necessarily be fully cylindrical, but may e.g. instead be formed by several radial webs or other structures. If the bearing surface is cylindrical, it need not necessarily extend all around the circumference of the guide element, but may be interrupted at one or more angular positions.

In order to avoid jamming, it is preferred that the length of the bearing surface is at least 1.5 times its diameter. For avoiding unnecessarily high resistance forces, it is preferred that the length of the bearing surface is not more than five times its diameter, preferably not more than three times the diameter.

In order to improve tactile feedback to the surgeon during injection, the plunger may be provided, on its perimeter, with a running surface (in other words, a bearing surface) having a radial distance from the central longitudinal axis which varies along the longitudinal axis. This running surface will then cooperate with a retaining element which is fixed relative to the main body with respect to movements along the longitudinal axis and which is radially movable and biased radially inwardly towards said running surface so as to exert a force on said running surface, causing a resistance force against axial movement of the plunger which depends on the axial position of the plunger relative to the main body. In other words, the retaining element will protrude inward to an extent which varies according to the axial position of the plunger due to the interaction with the running surface, this variation causing a variation in the resistance against movements of the plunger. Preferably the radial force exerted by the retaining element on the running surface itself varies, being the smaller the smaller is the distance of the running surface to the central longitudinal axis or to a central plane containing the longitudinal axis.

In particular, the running surface may comprise a depression for releasably holding the plunger in a predetermined intermediate position (e.g., in a so-called pre-load position) relative to the housing, the retaining element extending into said depression in the intermediate position so as to hinder movement of the plunger both in a distal and in a proximal direction. The depression may, e.g., be an at least partially circumferential groove.

The running surface may be formed by one or more lateral facets having a variable distance from a central plane containing the longitudinal axis. In particular, the running surface may comprise a first inclined portion or facet, the radial distance of the first inclined portion from the central plane continuously decreasing along the longitudinal axis in the proximal direction. The first inclined portion may be followed by a flat portion or facet having a substantially constant radial distance from the longitudinal axis. The flat portion may then be followed by a second inclined portion or facet, the radial distance of the second inclined portion from the longitudinal axis continuously or abruptly increasing along the longitudinal axis in the proximal direction.

The retaining element may be a spring-loaded sphere, in particular, a jewel sphere made, e.g., from sapphire or ruby, minimizing resistance forces. However, other types of spring-loaded elements, e.g. a nose on an elastically bendable arm, are conceivable.

In particular, the apparatus may comprise a cap connected to a proximal end of the main body, said cap having a sidewall portion and an end wall portion, the end wall portion covering a proximal end of said main body and having a through opening through which said plunger extends. The retaining element may then advantageously mounted on said cap. This simplifies assembly, disassembly and cleaning of the device.

In a second aspect, the present invention provides an apparatus for inserting an intraocular lens into an eye, comprising:

having a barrel portion defining a passage (which is preferably delimited by a cylindrical inner surface of a sidewall of the barrel portion) extending along a central longitudinal axis; and a plunger movably received in said passage, the plunger having a distal end and having a proximal end for manually pressing the plunger forward in the main body along the longitudinal axis, the plunger having, on its perimeter, a running surface having a radial distance from the longitudinal axis which varies along the longitudinal axis; and a retaining element which is fixed relative to the main body with respect to movements along the longitudinal axis and which is radially movable and biased radially inwardly towards said running surface so as to exert a force on said running surface, causing a resistance force against axial movement of the plunger which depends on the axial position of the plunger relative to the main body.

In other words, a running surface and the retaining element as described above may be present independently of the presence or absence of a guide element as described above. The running surface and the retaining element may have the properties described above in connection with the first aspect of the present invention.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

FIGS. 1-4 illustrate, in various views and states, a preferred embodiment of an IOL injector according to the present invention. The injector comprises an injector housing or injector main body 10 in which a plunger 50 is guided for longitudinal displacement along a central longitudinal axis L.

Main body 10 has a tubular barrel portion 11 defining a longitudinal lumen or passage 14 extending along the longitudinal axis L. Passage 14 is radially delimited by a substantially circumferential sidewall defining a cylindrical inner surface. A cartridge-receiving portion 12 distally adjoins barrel portion 11, extending away from barrel portion 11 in a distal direction. Cartridge-receiving portion 12 has structures such as hooks 13 for releasably holding a lens cartridge, in which an IOL can be provided for implantation into a patient's eye. Such cartridges are well known in the art and are widely used. Example of lens cartridges which might be used in conjunction with the presently described injector are described in U.S. Pat. No. 6,398,789, U.S. Pat. No. 6,143,001, U.S. Pat. No. 6,083,231 and U.S. Pat. No. 5,947,976, whose contents are incorporated herein by reference. The lens cartridge will generally have a lens-receiving portion retained in cartridge-receiving portion 12, and a nozzle portion extending distally beyond the distal end of main body 10. A lumen for receiving a plunger needle 80 connected to plunger 50 will generally extend through the lens-receiving portion and the nozzle portion. An intraocular lens provided in the lens-receiving portion of the cartridge may be pushed towards the nozzle portion and through an opening therein into a patient's eye by means of plunger needle 80. Depending on the type of lens cartridge, the lens is folded or rolled up during this process, or the lens may be already provided in a rolled-up or folded state in the lens receiving portion.

Figure 1:
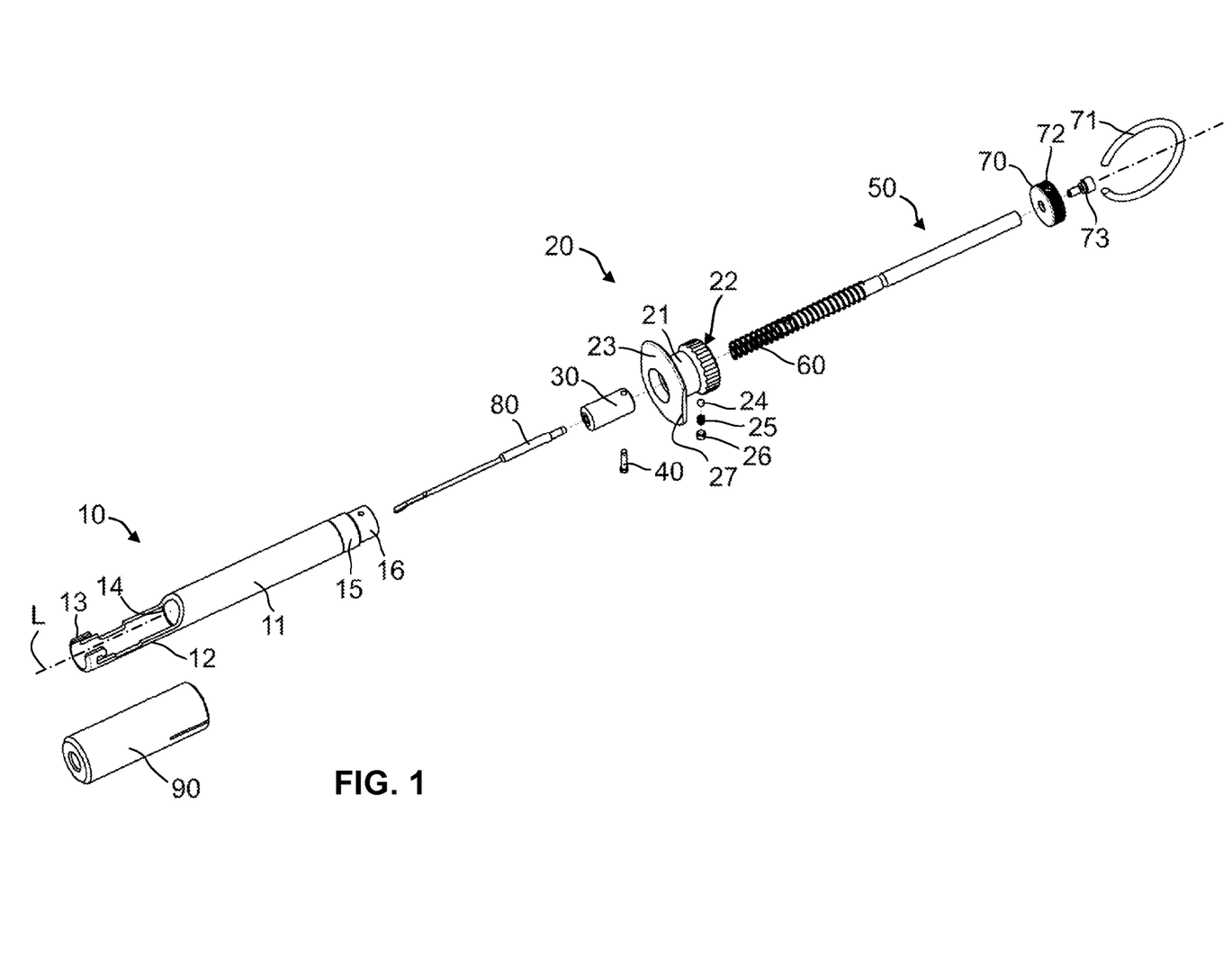
FIG. 1 shows an exemplary embodiment of an IOL injector according to the present invention in an exploded isometric view, together with a protecting sleeve.

Towards the proximal end of main body 10, an outer thread 15 is provided on barrel portion 11, the thread being shown only in a highly schematic fashion in FIG. 1. Thread 15 is adjoined by a reduced-diameter slip-on portion 16.

Main body 10 is preferably made from a corrosion-resistant and inert metal like titanium. However, it may also be envisaged to be manufactured from a high-strength plastic material.

Figure 2:
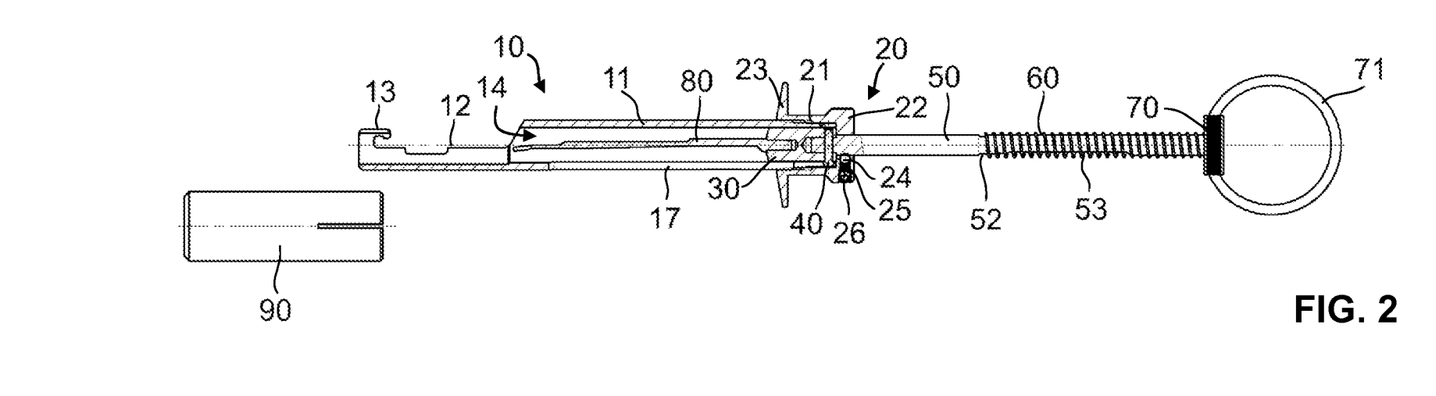
FIG. 2 shows the assembled injector of FIG. 1 in a configuration in which the plunger is fully retracted; the injector is generally shown in a side view, while the forward portion of the injector is shown in section along a plane extending centrally along the longitudinal axis and containing the handle ring.

A closure cap 20 having a circumferential sidewall 21 and a proximal end wall 22 is mounted on the proximal (rear) end of main body 10. The closure cap 20 may be considered to be a part of the main body 10. Closure cap 20 is slipped onto slip-on portion 16 of main body 10 and screwed onto main body 10 by means of an inner thread matching outer thread 15. In an alternative embodiment, closure cap 20 may be fixed on main body 10 with the aid of a stud or in any other suitable manner. At its distal end, closure cap 20 is provided with an annular lateral flange forming a finger support 23 for supporting the index and middle finger when a surgeon grips the injector in a manner like a syringe. To provide a stable support for the injector when the injector is laid on its side onto a flat horizontal surface like a tabletop, the annular flange has two radially opposite flattened lateral support surfaces 27. When the injector is laid down on its side, these support surfaces support the injector and prevent the injector from rolling. Instead of flattened surfaces, any other surface form providing at least two points of contact when the injector is laid on its side may be chosen, thereby ensuring support with a reduced risk of rolling. In particular, the support surfaces may be concave or may form at least two radial protrusions whose ends define a single plane. Instead of a single annular flange, two separate, radially opposite flanges or any other structure which may serve as a finger support may be provided. Instead of being formed on cap 20, the finger support may be a separate element, or it may be formed integrally with main body 10. End wall 22 is provided with a radial bore, in which a retaining element in form of a ruby sphere 24 is provided. Sphere 24 is elastically biased radially inside by means of a short coiled compression spring 25 held in position by a short stud 26.

Figure 5:
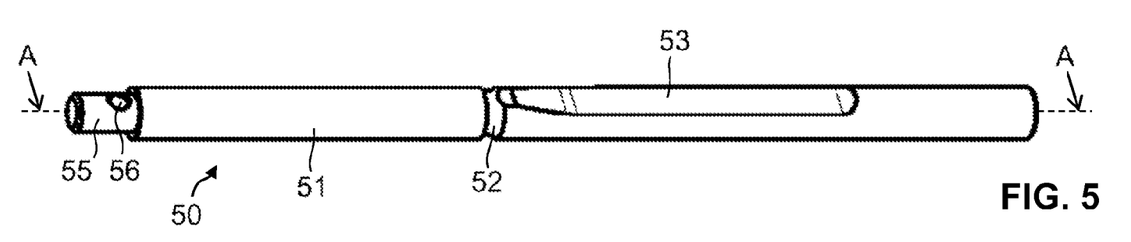
FIG. 5 shows the plunger of the injector of FIG. 1 in an enlarged isometric view.
Figure 6:
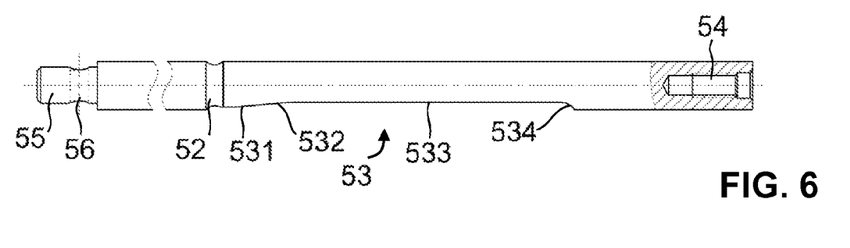
FIG. 6 shows the plunger in a central longitudinal sectional view in plane A-A of FIG. 5.

Plunger 50, which is shown in more detail in FIGS. 5 and 6, extends longitudinally through passage 14 of main body 10. Its proximal (rear) end portion protrudes from main body 10 through a central through opening in end wall 22 of closure cap 20. At the proximal end of plunger 50, a thumb pad 70 or plunger head serving as a support for a surgeon's thumb is mounted on plunger 50. In the present embodiment, thumb pad 70 is mounted on plunger 50 in a rotatable manner by means of a screw 73 received in a blind hole 54 of plunger 50, allowing for rotation of thumb pad 70 around longitudinal axis L. While this is particularly advantageous in specific situations, thumb pad 70 may also be rotationally fixed with respect to plunger 50 instead. An optional split handle ring 71 is inserted into lateral openings 72 of thumb pad 70 and acts to receive a surgeon's thumb. Handle ring 71 provides improved guidance of plunger 50 in main body 10 and enables a quick release of plunger 50 into its retracted position after insertion of the lens into the patient's eye. For further details and advantages of the handle ring, reference is made to U.S. Pat. No. 7,217,274, the contents of which are incorporated herein by reference in their entirety.

Plunger 50 is generally rod-shaped, having a generally cylindrical main portion 51, adjoined by a distal fastening portion 55 with reduced diameter as compared to main portion 51. At its proximal end, main portion 51 is provided with blind hole 54 having a female thread for receiving screw 73. A circumferential groove/depression 52 is formed in main portion 51. The groove is adjoined in the proximal direction by a plurality of lateral facets on the main portion 51, forming a running surface 53 having a distance from a central plane containing the plunger axis which varies along the length of the plunger. A first facet forms a short a first flat portion 531 with a first constant distance from the central plane. A second facet forms an inclined portion 532 of the running surface 52, the radial distance of the first inclined portion 532 from the central plane decreasing along the longitudinal axis in the proximal direction. The first inclined portion 532 is adjoined by a second flat portion 533 having a substantially constant radial distance from the longitudinal axis. The second flat portion 533 is then adjoined by a second inclined portion 534, the radial distance of the second inclined portion from the central plane increasing along the longitudinal axis in the proximal direction.

A coiled compression spring 60 surrounds plunger 50 between closure cap 20 and thumb pad 70 to provide controlled rearward (proximal) bias to plunger 50 against an advancement of plunger 50 in the distal direction.

Figure 7:
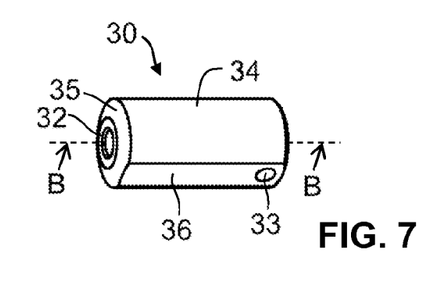
FIG. 7 shows the guide element of the injector of FIG. 1 in an isometric view.
Figure 8:
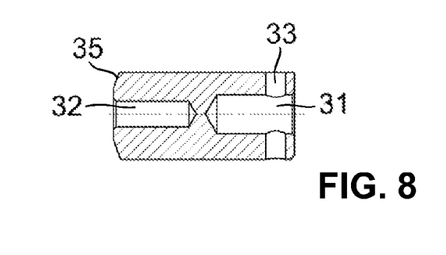
FIG. 8 shows the guide element in a central longitudinal sectional view in plane B-B of FIG. 7.

The distal (front) end of plunger 50 is connected to a guide element 30, which is shown in more detail in FIGS. 7 and 8. Guide element 30 has the form of a cylindrical plug or piston having an outer peripheral surface defining a cylindrical bearing surface 34, which is interrupted by a flattened surface portion 36. Towards the distal end of guide element 30, a bevel 35 is formed. Guide element 30 is provided with a first (proximal) axial bore 31 and a second (distal) axial bore 32, both bores taking the form of blind holes. In other embodiments, the bores may be connected and may form a through hole. A radial bore 33 extends through guide element 30, crossing first axial bore 31 and ending at flattened surface portion 36. The outer diameter of guide element 30 at bearing surface 34 closely matches the inner diameter of barrel portion 11 of main body 10. Thus bearing surface 34 is in direct contact with the inner surface of barrel portion 11, thereby establishing a linear friction bearing (linear plain bearing) between guide element 30 and main body 10 for guiding plunger 50 laterally during its axial movement relative to main body 10. In order to ensure a smooth movement without jamming, bearing surface 34 should have sufficient length as compared to its diameter. In the present example, the length of bearing surface 34 is approximately twice its length. Guide element 30 is preferably manufactured from a material having a low coefficient of friction with the material of main body 10. If main body 10 is manufactured from titanium, guide element 30 may be manufactured, e.g., from plastic materials such as PEEK.

For connecting plunger 50 to guide element 30, distal fastening portion 55 is received in first (proximal) axial bore 31 of guide element 30. Fastening portion 55 is held in bore 33 by a friction fit; however, other types of connection are conceivable, such as a threaded connection. Fastening portion 55 is provided with a radial bore 56, which is aligned with radial bore 33 of guide element 30. A guide pin 40 extends through both radial bores 33, 56 along the radial direction, thereby locking guide element 30 to plunger 50. Guide pin 40 is held in bores 33, 56 by a friction fit; however, other types of connection are conceivable, such as a threaded connection.

Figure 9:
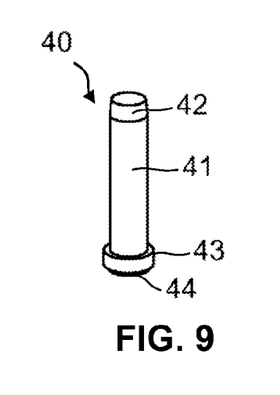
FIG. 9 shows the guide pin of the injector of FIG. 1 in an isometric view.
Figure 10:
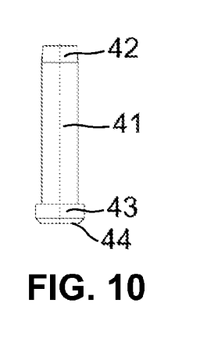
FIG. 10 shows the guide pin in a central longitudinal sectional view.

Guide pin 40 is shown in more detail in FIGS. 9 and 10. It has a cylindrical main portion 41 whose first end is provided with a bevel 42. Its second end is provided with a protruding flange portion 43, which likewise has a bevel 44. When guide pin 40 is inserted into guide element 30, flange portion 43 rests on flattened lateral surface portion 36 of guide element 30 and protrudes radially beyond the envelope of cylindrical bearing surface 34, extending into a longitudinal slot 17 in barrel portion 11 of main body 10. In this way, plunger 50 is secured against rotation or twisting about the longitudinal axis. For easy assembly, slot 17 is open towards the proximal end of main body 10, in the present example extending all the way to the proximal end of barrel portion 11 of main body 10. This makes it possible to first connect guide element 30 to plunger 50, to secure the connection by guide pin 40, and only then to insert guide element 30 into the proximal end of passageway 17 of main body 10 while flange portion 44 of guide pin 40 is received in the open proximal end of slot 17. The diameter of flange portion 44 is chosen to be slightly smaller than the width of slot 17. Instead of a slot, a groove may be provided on the inside of barrel portion 11, the groove likewise preferably being open towards the proximal end of main body 10.

For connecting plunger needle 80 to guide element 30, plunger needle 80 is provided with a proximal connecting portion 81 which is delimited towards the distal direction by a flange 82. The connecting portion preferably defines a keyed connection, e.g., by being flattened on one side. Connecting portion 81 is pushed into second (distal) bore 32 of guide element 30 and held in the bore by a friction fit. Other ways of connecting plunger needle 80 to guide element 30 are conceivable, such as a bayonet-type or twist-lock coupling similar to the one disclosed in US 2010/0305577 or a threaded connection. Plunger needle 80 ends in a specifically shaped tip for pushing the lens through the nozzle portion of the cartridge into the patient's eye. Protecting sleeve 90 serves to protect cartridge-receiving portion 12 and the tip of plunger needle 80 when no cartridge is inserted.

Figure 3:
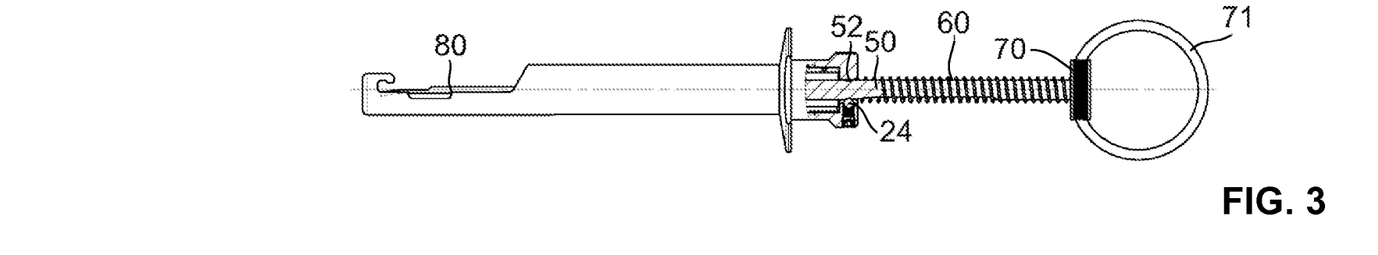
FIG. 3 shows the injector of FIG. 1 in a configuration in which the plunger has been advanced to a so-called pre-load position; the injector is generally shown in a side view, while portions of the injector are shown in section along the same plane as in FIG. 2.
Figure 4:
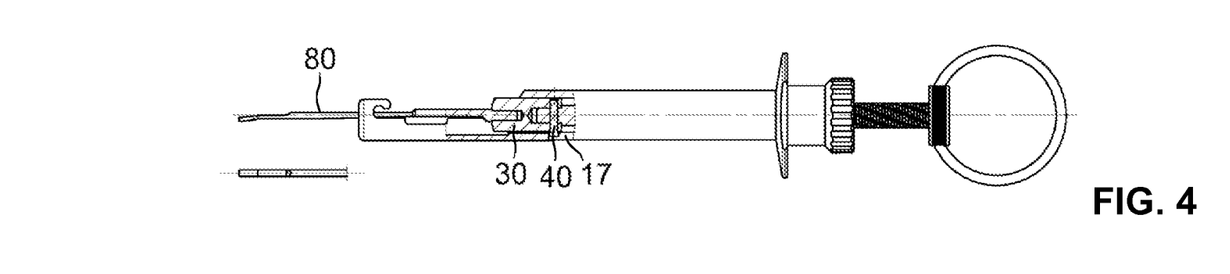
FIG. 4 shows the injector of FIG. 1 in a configuration in which the plunger has been fully advanced to an end position; again the injector is generally shown in a side view, while portions of the injector are shown in section along the same plane as in FIG. 2.
Figure 11:
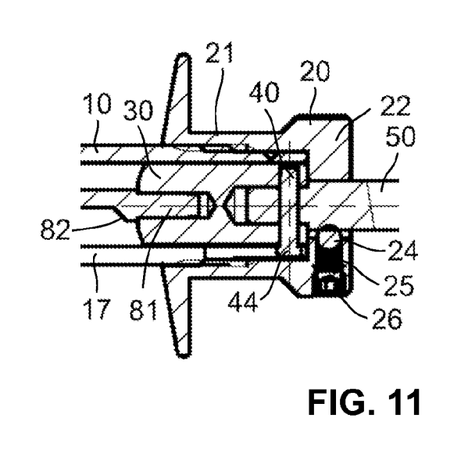
FIG. 11 shows a proximal main body end portion of the injector of FIG. 1 in a central longitudinal sectional view.

For operation of the device, plunger 50 is fully retracted until the proximal end of guide element 30 abuts to end wall 22 of closure cap 20. This situation is illustrated in FIG. 2 and is shown in greater detail in FIG. 11. A lens cartridge containing an intraocular lens for implantation is now inserted into cartridge-receiving section 12 of main body 10 and secured there by hooks 13. The surgeon holds the device by gripping main body 10 between his index and middle fingers in a manner that these fingers rest in front of finger support 23, and by inserting his thumb into handle ring 71 in a manner that the thumb rests on thumb pad 70. The surgeon then advances the plunger along the longitudinal direction until circumferential groove 52 on plunger 50 is in the same axial position as sphere 24. In this position of plunger 50, sphere 24 is pressed by spring 25 into circumferential groove 52, providing a resistance both against further advancement of plunger 50 in the distal direction as well as against a retraction of plunger 50 in the proximal direction. The spring acts against a cylindrical part of the main body 10 that surrounds the circumferential groove/depression. This situation, with plunger 50 in an intermediate or "pre-load" position, is shown in FIG. 3. The surgeon now knows that the lens has been forwarded within the cartridge by plunger needle 80 into the nozzle portion and is just about to exit the nozzle portion. He now inserts the nozzle portion into an incision in the patient's eye.

When plunger 50 is now further advanced for ejection of the lens, spring 60 starts to be compressed, exerting a rearward force to the plunger which slowly increases with further advancement of the plunger. Sphere 24 leaves groove 52 and now interacts with running surface 53. By the differently inclined portions or facets of running surface 53, the resistance of the plunger against further advancement is modified to improve tactile feedback to the surgeon. By the way of example, when sphere 24 interacts with first inclined portion 532, resistance against advancement of the plunger is decreased. This is the most critical phase when the lens is just about to be pressed through the nozzle portion of the cartridge. By appropriately shaping running surface 53, controlled feedback can be provided to the surgeon during advancement of the plunger, which aids the surgeon in carefully delivering the IOL into the patient's eye and in avoiding overshooting.

The plunger may be advanced against the biasing force of the spring until finally flange portion 43 of pin 40 abuts to the front end of slot 17, preventing the plunger from being forwarded any further. In this position, the lens has exited the nozzle portion of the cartridge, and further advancement of the plunger is prevented for avoiding damaging the patient's eye by the plunger tip.

LIST OF REFERENCE SIGNS 10 injector body
11 barrel portion
12 cartridge receiving portion
13 hook
14 bore
15 thread
16 slip-on portion
17 slot
20 cap
21 sidewall portion
22 end wall portion
23 finger support
24 sphere -continued

LIST OF REFERENCE SIGNS 25 spring
26 stud
27 flattened portion
30 guide element
31 proximal bore
32 distal bore
33 radial bore
34 bearing surface
35 bevel
36 flattened surface portion
40 guide pin
41 main portion
42 bevel
43 flange
44 bevel
50 plunger
51 cylindrical main portion
52 annular groove
53 lateral recess
531 first flat portion (facet)
532 inclined portion (facet)
533 second flat portion (facet)
534 arcuate end portion (facet)
54 bore
55 connecting portion
56 radial bore
60 compression spring
70 thumb pad
71 handle ring
80 plunger needle
81 connecting portion
82 stop flange
90 protecting sleeve

The invention claimed is:

1. An apparatus for inserting an intraocular lens into an eye, comprising:
a main body having a barrel portion defining a passage extending along a longitudinal axis; and
a plunger movably received in said passage, the plunger having a distal end and having a proximal end configured so that a user can directly apply an axial force to press the plunger forward in the main body along the longitudinal axis; and
a guide element at the distal end of said plunger, the guide element guiding the plunger in the barrel portion during movement along the longitudinal axis, the guide element having a proximal end and a distal end, and a plunger needle at the distal end of said guide element,
wherein the barrel portion of the main body is provided with a substantially longitudinal internal groove or with a substantially longitudinal slot, and wherein the guide element carries a stop element extending radially into said groove or slot so as to prevent twisting of the plunger relative to the main body,
the stop element moving guidingly longitudinally within the groove or slot as the plunger and main body are moved axially relative to each other,
wherein the plunger has, on its perimeter, an elongate running surface with a length that extends axially and having a radial distance from the longitudinal axis which varies along the longitudinal axis,
the apparatus further comprising a retaining element which is radially movable and biased radially inwardly towards said running surface so as to exert a force on said running surface, causing a resistance force against axial movement of the plunger which depends on the axial position of the plunger relative to the main body.

2. The apparatus of claim 1 wherein the guide element is an element separate from the plunger that is fixedly attached to the plunger.

3. The apparatus of claim 2, wherein the guide element has a radial bore, and wherein the stop element comprises a pin extending into said radial bore.

4. The apparatus of claim 3, wherein the plunger has a distal fastening portion connected to said guide element, the fastening portion having a radial bore in alignment with the radial bore of the guide element, and wherein the stop element extends both into the radial bore of the guide element and into the radial bore of the fastening portion so as to lock the plunger relative to the guide element.

5. The apparatus of claim 2, wherein the guide element and the barrel portion of the main body together form a linear friction bearing for the plunger.

6. The apparatus of claim 5, wherein the guide element has a cylinder portion defining a substantially cylindrical bearing surface, said bearing surface being in direct contact with an inner surface of the barrel portion of the main body.

7. An apparatus for inserting an intraocular lens into an eye, comprising:
- a main body having a barrel portion defining a passage extending along a longitudinal axis; and
- a plunger movably received in said passage, the plunger having a distal end and having a proximal end configured so that a user can apply an axial force to press the plunger forward in the main body along the longitudinal axis; and
- a guide element at the distal end of said plunger, the guide element guiding the plunger in the barrel portion during movement along the longitudinal axis, the guide element having a proximal end and a distal end, and a plunger needle at the distal end of said guide element,
- wherein the barrel portion of the main body is provided with a substantially, longitudinal internal groove or with a substantially longitudinal slot, and wherein the guide element carries a stop element extending laterally into said groove or slot so as to prevent twisting of the plunger relative to the main body,
- the stop element moving guidingly longitudinally within the groove or slot as the plunger and main body are moved axially relative to each other,
- wherein the guide element is an element separate from the plunger that is fixedly attached to the plunger,
- wherein the guide element comprises fastening structure to fasten the plunger needle to the distal end of the guide element, the fastening structure comprises a first longitudinal bore in the guide element, the first longitudinal bore being open towards the distal end of the guide element.

8. The apparatus of claim 7, wherein the guide element has a second longitudinal bore which is open towards the proximal end of the guide element, and wherein the plunger has a distal fastening portion extending into said second longitudinal bore.

9. An apparatus for inserting an intraocular lens into an eye, comprising:
- a main body having a barrel portion defining a passage extending along a longitudinal axis;
- a plunger movably received in said passage, the plunger having a distal end and having a proximal end configured so that a user can apply an axial force to press the plunger forward in the main body along the longitudinal axis; and
- a guide element at the distal end of said plunger, the guide element guiding the plunger in the barrel portion during movement along the longitudinal axis, the guide element having a proximal end and a distal end, and a plunger needle at the distal end of said guide element,
- wherein the barrel portion of the main body is provided with a substantially longitudinal internal groove or with a substantially longitudinal slot, and wherein the guide element carries a stop element extending into said groove or slot so as to prevent twisting of the plunger relative to the main body,
- the stop element moving guidingly longitudinally within the groove or slot as the plunger and main body are moved axially relative to each other,
- wherein the plunger has, on its perimeter, an elongate running surface with a length that extends axially and having a radial distance from the longitudinal axis which varies along the longitudinal axis,
- the apparatus further comprising a retaining element which is fixed relative to the main body with respect to movements along the longitudinal axis and which is radially movable and biased radially inwardly towards said running surface so as to exert a force on said running surface, causing a resistance force against axial movement of the plunger which depends on the axial position of the plunger relative to the main body,
- the plunger and retaining element configured to cooperate, with the plunger and retaining element in a first predetermined axial relationship, to hinder movement of the plunger axially relative to the retaining element both in distal and proximal directions.

10. The apparatus of claim 9, wherein said running surface comprises a depression formed by a circumferential groove extending around the plunger at an axial location on the plunger for releasably holding the plunger in a predetermined intermediate position relative to the main body with the plunger and retaining element in the first predetermined axial relationship, the retaining element extending into said depression with the plunger in the intermediate position so as to hinder movement of the plunger both in a distal and in a proximal direction.

11. The apparatus of claim 9, wherein said running surface has a first inclined portion, the radial distance of the first inclined portion from a central plane containing the longitudinal axis continuously decreasing along the longitudinal axis in the proximal direction.

12. The apparatus of claim 11, wherein said first inclined portion is followed by a flat portion having a substantially constant radial distance from the central plane.

13. The apparatus of claim 12, wherein said flat portion is followed by a second inclined portion, the radial distance of the second inclined portion from the central plane increasing along the longitudinal axis in the proximal direction.

14. The apparatus of claim 9, wherein the retaining element is a spring-loaded sphere.

15. The apparatus of claim 9, further comprising a cap connected to a proximal end of the main body, said cap having a sidewall portion and an end wall portion, the end wall portion covering a proximal end of said main body and having a through opening through which said plunger passes, the retaining element being mounted on said cap.

16. An apparatus for inserting an intraocular lens into an eye, comprising:
- a main body having a barrel portion defining a passage extending along a longitudinal axis; and
- a plunger movably received in said passage, the plunger having a proximal end and a distal end for manually moving the plunger forward in the main body along the longitudinal axis through the application of an axial force by a user, the plunger having, on its perimeter, an elongate running surface with a length that extends axially and having a radial distance from the longitudinal axis which varies along the longitudinal axis, the apparatus further comprising a retaining element which is fixed relative to the main body with respect to movements along the longitudinal axis which is radially movable and biased radially inwardly towards said running surface so as to exert a force on said running surface, causing a resistance force against axial movement of the plunger which depends on the axial position of the plunger relative to the main body, the plunger and the retaining element, in a first determined axial relationship, configured to cooperate to hinder movement of the plunger axially relative to the retaining element both in distal and proximal directions, wherein with the plunger and retaining element in the first predetermined axial relationship, a depression on the running surface releasably holds the plunger in a predetermined intermediate position relative to the main body, the retaining element extending into said depression with the plunger in the intermediate position so as to hinder movement of the plunger both in a distal and in a proximal direction, the main body comprising a cylindrical portion extending around the depression and the retaining element is biased radially inwardly from the cylindrical portion into the depression.

17. The apparatus of claim 16, wherein said running surface has a first inclined portion, the radial distance of the first inclined portion from a central plane containing the longitudinal axis continuously decreasing along the longitudinal axis in the proximal direction, the plunger and retaining element configured so that the retaining element moves axially relative to the first inclined portion so as to thereby vary a force exerted by the retaining element on the plunger.

18. The apparatus of claim 17, wherein said first inclined portion is followed by a flat portion having a substantially constant radial distance from the central plane.

19. The apparatus of claim 18, wherein said flat portion is followed by a second inclined portion, the radial distance of the second inclined portion from the central plane increasing along the longitudinal axis in the proximal direction, the plunger and retaining element configured so that the retaining element moves axially relative to the second inclined portion so as to thereby vary a force exerted by the retaining element on the plunger.

20. The apparatus of claim 16, wherein the retaining element is a spring-loaded sphere.

21. The apparatus of claim 16, wherein the main body further comprises a cap connected to a proximal end of the main body, said cap having a sidewall portion defining said cylindrical portion, extending around the depression, and an end wall portion, the end wall portion covering a proximal end of said main body and having a through opening through which said plunger passes.

22. The apparatus of claim 16 wherein the plunger and main body are configured so that the plunger is movable guidingly axially relative to the main body without turning around the longitudinal axis.

* * * * *